United States Patent [19] [11] Patent Number: 4,838,861
Sharp [45] Date of Patent: Jun. 13, 1989

[54] BLOOD PRESERVATION BY ULTRAHEMODILUTION

[76] Inventor: David E. Sharp, 36032 Derby Downs, Solon, Ohio 44139

[21] Appl. No.: 858,740

[22] Filed: May 2, 1986

[51] Int. Cl.$^4$ ............................................. A61M 37/00
[52] U.S. Cl. ............................................. 604/6; 604/5
[58] Field of Search ........................................ 604/4–6

[56] References Cited

U.S. PATENT DOCUMENTS 4,531,932 7/1985 Luppi et al. ............................. 604/6

OTHER PUBLICATIONS

Jobes & Gallagher, *Acute Normovolemic Hemodilution*, 0020—5907/82/040077—19, 1981, pp. 77–95.
Solem, Steen, & Olin, *A New Method For Autotransfusion Of Shed Blood*, Acta Chir Scan, 152:421–425, 1986.
Solem, Tengborn, Olin, & Steen, *Autotransfusion Of Whole Blood In Massive Bleeding*, Acta Chir Scan, 152:427–432, 1986.
Sohmer, MD & Schiffer, MD, *Blood Storage & Preservation A Technical Workshop*, 1982, pp. 42–62.

*Primary Examiner*—Stephen C. Pellegrino
*Assistant Examiner*—Kathleen A. Daley
*Attorney, Agent, or Firm*—Browdy and Neimark

[57] ABSTRACT

The storage of blood and the prevention of coagulation are effected by diluting freshly drawn blood with either isotonic saline or isotonic saline including preservatives and subtherapeutic amounts of heparin. The present method of storing blood is especially useful for autotransfusion and storage of blood for subsequent fractionation or analysis of aliquots thereof.

11 Claims, No Drawings

BLOOD PRESERVATION BY ULTRAHEMODILUTION

FIELD OF INVENTION

This invention relates generally to blood processing and more specifically to the prevention of coagulation in blood samples.

BACKGROUND OF THE INVENTION

It is well known that stored blood has for many years been quite effective in saving lives. Of course, difficulties in storing blood samples and blood components limit the use of stored blood.

A major problem with storing blood is the tendency for blood to coagulate after removal from a patient. For this reason, anticoagulant agents are added to blood immediately after its removal from a patient or a donor. The anticoagulants include more heparin, an antithrombin III cofactor and chelating agents such as trisodium citrate. While these agents have been generally effective, they each present disadvantages. For example, anticoagulants including heparin and citrate allow deteriorization of sensitive blood components, especially plasma clotting factors.

Heparin, of course, remains in the blood of a patient into which it has been infused, and may therefore increase the risk of bleeding until sufficient metabolism of heparin has occurred. Citrate is minimally toxic in high concentration and is readily metabolised by the liver into lactic acid which is then excreted. Therefore, in most cases, citrated blood or plasma is safe for infusion. However, in patients with significant liver damage, or where large amounts of citrated blood are rapidly infused, the patient may be unable to convert citrate to lactic acid at a sufficient rate and indeed death may result. Additionally, citrated blood containing added glucose may precipitate hyperglycemic shock in patients with glucose intolerance.

A large number of transfusions are performed under emergency conditions. During an emergency, hospital staff may be unable to determine whether the patient has a glucose intolerance or liver dysfunction prior to the time when transfusion must be performed. Accordingly, a strong need exists for a method which preserves blood in a form which can safely be infused into almost any patient.

The ability of normal saline to progressively prolong the coagulation time in vitro when added to blood in increasing amounts was first described by Copley and Houlihan in 1944 (Science 100: 505, 1944). Later they employed saline dilution of blood in a ratio of 1 part blood to 9 parts saline or 1 part blood to 14 parts saline to render the blood incoagulable. Paradoxically, Toscantins et al found that dilution of blood or plasma increased the rate of coagulation (Blood 6: 720-39, 1951). The biphasic effect of dilution of blood with saline was confirmed by Heather et al who demonstrated maximal coagulability at between 75 and 85 percent blood concentration with decreased coagulability at 70 percent blood concentration (British Journal of Surgery 67: 63-65, 1980). Current practices in surgery on the heart include hemodilution with cystalloid solutions to moderate levels (hematocrit of 30) and to extreme levels (hematocrit to 18).

While, as set forth above, it has been previously recognized that ultrahemodilution with isotonic saline can prevent coagulation, there have been no reports concerning the viability of ultrahemodiluted blood. Additionally, since storage space is increased by ultrahemodilution, there has been little incentive for those skilled in the art to conduct further research along these lines.

Moreover, ultrahemodiluted blood has sufficient oxygen carrying capacity to support homeostasis. There has been no prior recognition that ultrahemodiluted blood could be simply and inexpensively separated and concentrated back to a normal concentration capable of supporting homeostasis. Although, minimally diluted blood has been passed through heart-lung machines, the diluted blood remained capable of supporting homeostasis since the degree of blood dilution was within normal biological limits.

As the capacity of ultrafiltration is a function of the degree of hemodilution, the number of filters, and the filtration rate, the permissible degree of hemodilution cannot specifically be set forth.

Also, blood drawn from a patient often needs to be analyzed in a clinical laboratory for various purposes. Under all circumstances, it is desirable to minimize the actual amount of blood drawn. Nevertheless, accurately handling and transferring extremely minute amounts of liquid accurately can be difficult and expensive. Further, for increased accuracy, more than one sample per test or measurement is preferred.

SUMMARY OF THE INVENTION

It is an object of the present invention to overcome deficiencies in the prior art, such as indicated above.

It is another object of the present invention to improve the storability of blood.

It is a further object of the present invention to provide a method for storing blood which does not require anticoagulant additives.

It is yet another object of the present invention to provide a method for storing blood which does not significantly damage labile blood components.

It is yet a further object of the present invention to provide a process for storing blood which facilitates handling of the blood during subsequent analysis.

These and other objects are achieved by diluting a blood sample drawn from a patient at least 10-fold with a solution of isotonic saline. If the blood is to be processed to form packed or washed red cells, the diluted blood may be centrifuged, the plasma and diluent decanted, and the red blood cells may be used or further washed with fresh saline as is usually done. If the blood is to be infused into the same or a different patient, then the blood is reconcentrated to within a concentration range capable of supporting homeostasis by membrane filtration. If testing is to be performed upon the blood, the diluted blood sample is divided into a number of aliquots and the composition of these aliquots analyzed by conventional, highly sensitive means.

DESCRIPTION OF THE PREFERRED EMBODIMENTS

While blood is drawn from the patient, the blood is diluted at least ten-fold with a solution of isotonic saline. The exact composition of this solution may vary depending upon circumstances, but the precise composition of isotonic saline solutions is well known in this field. As one common example, in the experiments below, the 100 ml. of solution contained 900 mg of sodium chloride, approximate pH 5.0. approximate m Osmol/L.

of 308. Human blood drawn from the antecubital vein of a healthy donor using a 21 gauge butterfly needle into a 10 cc. plastic syringe clotted within 16 minutes when agitated by inversion with an air bubble present. Similarly, blood drawn into 5 volumes of the solution clotted within 3 hours, but blood drawn into 10 volumes of the solution did not clot within 72 hours.

The results of a second experiment are shown in Table 1. Appropriate control blood samples were drawn in trisodium citrate or EDTA anticoagulants.

TABLE 1

|  | WBC | RBC | HGB | HCT | PT | PTT |
|---|---|---|---|---|---|---|
| 1:5 Vol. Hemodiluted Blood | 1.5 | 0.89 | 3.0 | 8.6 | 24.2 | 71.8 |
| 1:10 Vol. Hemodiluted Blood | 1.1 | 0.49 | 1.6 | 4.7 | 38.2 | 246 |
| Trisodium Citrate Control | — | — | — | — | 11.5 | 28.9 |
| EDTA Control | 7.1 | 5.32 | 16.8 | 51.2 | — | — |

WBC - White Blood Cells ($\times 10^3$/microliter)
RBC - Red Blood Cells ($\times 10^6$/microliter)
HGB - Hemoglobin (G/dl)
HCT - Hematocrit (%)
PT - Prothrombin Time (Sec.) Mean
PTT - Partial Thromboplastin Time (Sec.) Mean —;

If the blood is to be infused into the same or a different patient within the next few hours, the solution should contain only isotonic saline, or isotonic saline and whatever therapeutic agents (other than therapeutic amounts of anticoagulants or other blood extenders) may be helpful for the recipient's recovery. The diluted blood, just prior to infusion, should be returned to essentially its original constituency by conventional membrane filtration to remove the diluent isotonic saline. If the blood is to be processed into components, such as washed red blood cells, then the composition of the solution may depend on what component is desired and the time span over which processing into fractions will take place. If labile plasma components are sought or processing will be completed in a matter of hours, then the diluent solution should be only isotonic saline. If processing will take more than 4 to 6 hours, preserving agents, such as those described in U.S. Pat. No. 4,267,269 to Grode et al., incorporated herein by reference, including adenine, glucose, fructose and mannitol, might be used. Subtherapeutic amounts of heparin (below the amount required to prevent coagulation) may also be added to ultrahemodiluted blood to counteract thrombin activation.

The ultrahemodiluted blood may also be processed into components such as cryoprecipitate or fresh frozen plasma other than washed red blood cells by conventional processing means. The components may be usually pure, since undesirable contaminants such as thrombin have been inhibited or diluted by the ultrahemodilution. Also, if processing occurs within 4 to 6 hours of the drawing of the blood, and the ultrahemodiluted blood has been stored at temperatures conventionally used for preserving the desired component fractions, each component should be highly active, since no potentially harmful blood preservatives need be present in the ultrahemodiluted blood. Of course, pH sensitive components of the red blood cells such as 2–3 diphosphaglycerate may be protected by the addition of a buffer, to provide a physiological or otherwise appropriate pH.

As stated above, for transfusion the blood may be concentrated to near its original concentration by membrane filtration at the time of collection or just prior to infusion into the patient.

Although it is not intended that the invention be bound by any particular theory, it is believed that the method by which the present invention prevents coagulation is by reducing the calcium concentration to below that sufficient or necessary for initiation of coagulation. To a much lesser, and perhaps an insignificant extent, the dilution of blood clotting factors may also reduce the tendency of ultrahemodiluted blood to coagulate.

When blood is drawn and diluted for further analysis, it may be helpful to add an inert tracer composition, not absorbed into blood cells, at a known concentration to the blood prior to dilution. Tracer compositions meeting these criteria are already known to those skilled in the art. These tracer components provide a convenient means for the analyzing laboratory to recognize the dilution factor of an analyzed sample.

As used in the present specification and claims, the term "supporting homeostasis" means maintaining normal biological functioning with no more than conventional cardio-pulmonary support.

Obviously, many modifications and variations of the present invention are possible in light of the above teachings. It is, therefore, to be understood that the invention may be practiced otherwise than as specifically described.

What is claimed is:

1. A method of storing blood comprising the steps of:
   diluting blood from a mammal by at least about 10 fold without a solution consisting essentially of isotonic saline;
   storing said diluted blood;
   centrifuging said diluted blood to form a plasma fraction and a red blood cell fraction;
   separating said fractions;
   reconstituting one of said fractions to produce a reconstituted blood product capable of supporting homeostasis in said mammal; and
   infusing said reconstituted blood product to a mammal.

2. The method of claim 1 wherein said solution consists of isotonic saline.

3. The method of claim 1, wherein said solution includes a buffering amount of a physiological buffer.

4. The method of claim 3 wherein said physiological buffer is a phosphate buffer.

5. The method of claim 3 wherein said physiological buffer is a bicarbonate buffer.

6. The method of claim 1 wherein said solution includes a member selected from the group consisting of a subtherapeutic concentration of heparin, a pharmacologically effective concentration of adenine, a pharmacologically effective concentration of glucose, a pharmacologically effective concentration of fructose, and a pharmacologically effective concentration mannitol.

7. A method of temporarily storing blood for infusion into a patient, comprising the steps of:
   diluting blood by at least about ten-fold with a solution consisting essentially of isotonic saline;
   storing said diluted blood;
   filtering said diluted blood to remove said diluent isotonic saline and restoring said blood to a concentration capable of supporting homeostasis in said patient;
   infusing said restored blood into said patient.

8. The method of claim 7 wherein said solution consists of isotonic saline.

9. The method of claim 7 wherein said solution includes a buffering amount of a physiological buffer.

10. The method of claim 7 wherein said physiological buffer is a phosphate buffer.

11. The method of claim 7 wherein said solution includes a member selected from the group consisting of a subtherapeutic concentration of heparin, a pharmacologically effective concentration of adenine, a pharmacologically effective concentration of fructose, and a pharmacologically effective concentration of mannitol.

* * * * *